United States Patent [19]

Marks

[11] 4,247,547
[45] Jan. 27, 1981

[54] TRETINOIN IN A GEL VEHICLE FOR ACNE TREATMENT

[75] Inventor: Alan M. Marks, East Brunswick, N.J.

[73] Assignee: Johnson & Johnson, New Brunswick, N.J.

[21] Appl. No.: 22,022

[22] Filed: Mar. 19, 1979

Related U.S. Application Data

[63] Continuation of Ser. No. 541,906, Jan. 17, 1975, abandoned.

[51] Int. Cl.$^3$ .................... A61K 31/20; A61K 31/56
[52] U.S. Cl. .................... 424/240; 424/81; 424/318; 424/344; 424/362
[58] Field of Search ................ 424/318, 344, 240

[56] References Cited

U.S. PATENT DOCUMENTS

| | | | |
|---|---|---|---|
| 3,729,568 | 4/1973 | Kligman | 424/318 |
| 3,867,533 | 2/1975 | Schmolka | 424/318 |

OTHER PUBLICATIONS

Konig et al., Arzneimitt-Forsch, No. 8 (1974) 1184–1187.
Hopponen, Handbook of Non-Prescription Drugs, pp. 155–160 (1973).
Martin, Physical Pharmacy, pp. 623–627 (1962).
Physicians Desk Reference (PDR) 1968, pp. 1108 & 1214.

*Primary Examiner*—Leonard Schenkman
*Attorney, Agent, or Firm*—Irving Newman

[57] ABSTRACT

An acne treatment gel composition, effective at low concentrations of tretinoin, is provided for topical application. The composition is highly effective in treating acne conditions and is capable of being stored without refrigeration for long periods of time without losing therapeutic effectiveness and while maintaining the uniformity and stability of the gel.

10 Claims, No Drawings

TRETINOIN IN A GEL VEHICLE FOR ACNE TREATMENT

CROSS-REFERENCE TO RELATED APPLICATION

This application is a continuation of my copending application Ser. No. 541,906, filed Jan. 17, 1975, now abandoned.

BACKGROUND OF THE INVENTION

1. Field of the Invention

The invention relates to a gel formulation of tretinoin (all trans-retinoic acid, or vitamin A acid). More particularly, it relates to gel formulations of tretinoin which are effective when tretinoin is present in low concentrations. The product is particularly suitable for treating such dermatological disorders as acne vulgaris.

2. Description of the Prior Art

Acne vulgaris is a dermatological disorder prevalent in adolescence. It appears most commonly on the face and trunk of the patient. The basic lesion of acne is the comedo or "blackhead" of a pilosebaceous follicle. In its mildest form, only few comedones are present, but in its severe form, a multiplicity of severe, persistent comedones are present. Permanent scarring is frequently a consequence of the severe form of acne.

Acne occurs when there is a filling up of the follicle with a rather tough keratinous material. This impaction of horny material is the whitehead and blackhead. As a result of bacterial growth in these horny impactions, the follicle ruptures, initiating the inflammatory phase of the disease which takes the form of pustules, papules, cysts and nodules.

A variety of methods have been used for the treatment of acne, including the use of peeling agents, hormone therapy for female patients, antibacterial therapy and general surgical skin planing.

Although the systemic administration of hormones and antibacterials have been used with some success, until recently none of the topical treatments have been particularly effective.

Vitamin A acid (tretinoin) has been applied topically, (Beer, Von P., "Untersuchungen über die Wirkung der Vitamin A-Säure," *Dermatologica*, 124: 192-195, March, 1962 and Stüttgen, G., "Zur Lakalbehandlung von Keratosen mit Vitamin A-Säure," *Dermatologica*, 124: 65-80, February, 1962) in those hyperkeratotic disorders which are responsive to high oral doses of Vitamin A. Among those treated by Beer and Stüttgen were patients with acne; however, these investigators reported no effective results with Vitamin A acid on acne. British Pat. No. 906,000 disclosed a cosmetic preparation containing Vitamin A acid for the regulation of the cornification processes of human skin, but no mention is made of the use of such preparation for the treatment of acne.

Recently, however, it has been demonstrated that prolonged topical application of Vitamin A acid is effective in the treatment of acne (Kligman, A. M., "Topical Vitamin A acid in Acne Vulgaris," *Arch Derm.*, 99: 469-476 April 1969). Kligman utilizes a composition in which Vitamin A acid is dispersed in a water-miscible (substantially oil- and fat-free) liquid carrier having high solvating action. The topical application of this Vitamin A acid composition causes irritation of the skin in the treated areas. See U.S. Pat. No. 3,729,568 issued Apr. 24, 1973 to Albert M. Kligman.

More recently, it has been found that acne can be effectively treated with a cream formulation containing tretinoin, or Vitamin A acid. A cream formulation is generally more acceptable to patients than the liquid vehicle from the point of view of aesthetics and ease of application. Moreover, another important advantage of the cream form of tretinoin is that it reduces the side effects normally associated with the topical application of tretinoin. These side effects, erythema, stinging and itching, may be sufficient to cause the patient to discontinue the application of tretinoin before it can be fully effective upon the acne.

Notwithstanding these advantages, cream formulations containing tretinoin possess some undesirable attributes. One of these undesirable attributes is the difficulty in uniformly applying sufficient amounts of the active ingredient to the lesion of acne to be effective and at the same time avoid local excesses, surface spread or pooling into facial creases, the nasolabial folds and corners of the mouth where the cream may cause erythema, stinging and itching. Another undesirable attribute of cream formulations of tretinoin is their relative instability, often necessitating the use of refrigeration or antimicrobial preservatives to prevent microbiological contamination, as well as special additives to maintain physical stability.

It is, therefore, an object of the present invention to provide a vehicle for tretinoin from which tretinoin is readily available for absorption by the skin.

It is a further object to provide an acne treatment composition which is effective at low concentrations of tretinoin, so as to avoid side effects associated with the use of acne treatment formulations having high concentrations of tretinoin.

It is another object of the invention to provide gel formulations of tretinoin which possess good physical and chemical stability without refrigeration and without special additives or antimicrobial preservatives.

It is still another object to provide gel formulations having such other desirable qualities as being cosmetically elegant, having a perceptible drying effect or at least making no contributions to the oiliness of acne patients' skin, and allowing accurate application of effective amounts of tretinoin to the acne lesion.

These and other objects of the present invention will be more fully understood in the light of the specific examples and description set forth hereinafter.

SUMMARY OF THE INVENTION

In general, my invention comprises a gel formulation containing a therapeutically effective amount of tretinoin (all trans-vitamin A acid; retinoic acid); an organic solvent for the tretinoin selected from the group consisting of ethanol (absolute or 95% by volume ethyl alcohol), isopropanol, propylene glycol and combinations thereof; an antioxidant selected from the group consisting of butylated hydroxytoluene (BHT), butylated hydroxyanisole (BHA), ascorbic acid (Vitamin C), propyl gallate, and α-tocopherol (Vitamin E); and a gelling agent selected from the group consisting of (1) an acidic carboxy polymer, such as those available under the trade names Carbopol 934 and Carbopol 940, neutralized with an organic amine, (2) hydroxyethylcellulose and (3) hydroxypropyl cellulose. Other conventionally used ingredients may be added, if desired, such as dyes, perfumes, sunscreens, antimicrobials and topical corticosteroids.

A general formula encompassing tretinoin gel formulations within the scope of my invention is set forth below. (Unless otherwise indicated herein, all amounts are in weight percent.)

| General Gel Formula in % w/w | |
| --- | --- |
| Tretinoin | 0.001–0.500 |
| Antioxidant(s) | 0.010–0.100 |
| Gelling agent(s) | 0.5–5.000 |
| Dye(s) and/or perfume oil(s) | 0.0–0.750 |
| Sunscreen(s) | 0.0–2.500 |
| Topical corticosteroid | 0.0–2.000 |
| Antimicrobial(s) | 0.0–3.000 |
| Organic solvent | q.s. to 100.000 |

It has been unexpectedly found that tretinoin gel formulations of the present invention are more effective in the treatment of acne conditions than tretinoin cream formulations of similar tretinoin concentration. It also has been found that cream formulations having low concentrations of tretinoin may have little or no efficacy against acne when compared to the same vehicle with no tretinoin, whereas, gel formulations having the same low concentrations of tretinoin exhibit high efficacy against acne, the efficacy level often being almost the same as exhibited by gels with higher tretinoin concentrations. This is a surprising and unexpected discovery and the reason for it is not fully understood. However, without the intention of being bound by it, the following explanation is provided.

It is known in the healing art that solid drugs intended for absorption by the skin are not absorbed directly but must be dissolved by a vehicle or by skin fluids. It is also well known that drugs in the microfine form are more readily available for absorption. Upon evaporation of the solvent carrier drugs are deposited on the skin in different forms, such as, for example large crystals or a film. Tretinoin is not soluble in common vehicles such as, for example, water. It is soluble in several vehicles if the vehicles are made alkaline. However, in alkaline solutions tretinoin is very unstable. The only vehicles in which tretinoin is both soluble and at the same time stable are the organic solvents. Most of these organic solvents quickly evaporate and leave behind the large crystalline deposit of tretinoin. It is then up to the skin fluids to solvate the crystalline tretinoin for absorption by the skin. The rate of absorption mainly depends on the solubility of tretinoin in skin fluids. Obviously, the larger the crystals, the lower their solubility in skin fluids and the slower their absorption through the skin. It is believed that the tretinoin is deposited on the skin from the gel formulations of the present invention in a microfine form, thus promoting the penetration of tretinoin through the skin by virtue of its relative ease of solubility in skin fluids as compared to that of a larger crystal form. This would enable a lower strength tretinoin gel to deliver subcutaneously an effective quantity of the tretinoin that is equivalent to that delivered by a preparation of higher strength from which the tretinoin is not deposited on the skin in a micro-fine form.

Tretinoin gel formulations in accordance with the present invention have been found to have good chemical and physical stability for at least 18 months at 100° F.

DETAILED DESCRIPTION OF THE INVENTION

A tretinoin gel formulation of the present invention, in general, comprises from about 0.001 weight % to about 0.500 weight % of tretinoin; from about 0.01 weight % to about 0.10 weight % of an antioxidant selected from the group consisting of butylated hydroxytoluene (BHT), butylated hydroxyanisole (BHA), ascorbic acid (Vitamin C), propyl gallate and α-tocopherol (Vitamin E); from about 0.5 to about 5.0 weight % of a gelling agent selected from the group consisting of hydroxyethylcellulose, hydroxypropyl cellulose, and an acidic carboxy polymer such as the ones available under the trade name Carbopol 934 and Carbopol 940, which is neutralized with an organic amine, such as, β-alanine or diisopropanol amine; and from about 84 to 99 weight % of a solvent selected from the group consisting of ethanol, isopropanol, propylene glycol and combinations thereof. Optionally, minor amounts of such agents as dyes, perfumes, and sunscreens which are commonly used in topical pharmaceutical compositions may be added. Furthermore, such topically active medicaments as the anti-inflammatory corticosteroids and antimicrobials may also be incorporated.

While the tretinoin gel compositions of the present invention have been described herein primarily as suitable for use in treating acne, it will be understood that these compositions are effective generally for treating dermatological conditions where tretinoin is indicated. The concentration of tretinoin in the gel compositions of the present invention may be as low as 0.001 or 0.0025 weight %. The preferred range for the concentration of tretinoin in the gel formulation is from about 0.005 to about 0.05 weight %, from about 0.01 to about 0.025 weight % being particularly preferred. Besides being effective and safe on application to the skin, concentrations within these preferred ranges offer substantial costs savings.

The antioxidants which may be used in the compositions of the present invention are those which are soluble in ethanol, isopropyl alcohol, propylene glycol and mixtures thereof; are non reactive to the gelling agents, tretinoin, and other components of the formulations; and are safe for human topical use. I prefer to employ from about 0.025 to about 0.075 weight % of an antioxidant selected from the group consisting of butylated hydroxytoluene (BHT), butylated hydroxyanisole (BHA), ascorbic acid (Vitamin C), propyl gallate, and α-tocopherol (Vitamin E), although other antioxidants may be used provided they satisfy the above criteria.

The gelling agents employed in the compositions of the present invention are those capable of being solvated or those which can be modified to be capable of being solvated in the solvents utilized in these compositions and which are commonly used in pharmaceutical preparations for topical applications. While there are numerous pharmaceutically acceptable gelling agents for topical use, they are either only marginally acceptable such as, for example, ethyl cellulose or they are not suitable for the purposes of the present invention such as, for example, methylcellulose and the salts and derivatives of alginic acid because they do not form a satisfactory gel. I prefer to use amounts of from about 0.5 to about 3.0 weight % of a gelling agent selected from the group consisting of hydroxyethylcellulose, having a viscosity of from about 3,500 to about 50,000 cps. when a 2 percent aqueous solution is measured at 20° C. using Brookfield Viscometer, Model LVF, with Spindle #30 at 30 RPM., available under the trade name Natrosol from Hercules Powder Co., Inc., Wilmington, Delaware; hydroxypropyl cellulose having a molecular weight from about 100,000 to about 1,000,000, available under the trade name Klucel from Hercules Powder Co. Inc.; an acidic carboxy polymer, such as those available under the trade names Carbopol 934 and Carbopol 940 from B. F. Goodrich Chemical Co., Cleveland, Ohio, neutralized with an organic amine, such as β-alanine or diisopropanol amine. The neutralization of the acidic carboxy polymer with an organic amine enables the acidic carboxy polymer to be solvated by the organic solvent utilized in practicing the invention. While partial neutralization is sufficient to effect solvation, preferably the amount of organic amine used to neutralize the acidic carboxy polymer will generally be approximately equivalent by moles to the acidic carboxy polymer present in the formulation, and may even be in excess of the molar equivalent amount.

While many organic solvents could be used to solubilize tretinoin, ethanol, isopropanol, propylene glycol and mixtures thereof are particularly preferred for reasons related to toxicity, irritation and quality of product made therewith. As indicated previously, the solvents form the largest part by weight of the compositions of the present invention and are generally present in amounts of from about 84 weight % to about 99 weight %.

The compositions of the invention may be prepared by various methods practiced and well known in the art. In general, the formula amount of antioxidant is dissolved in the solvent, followed by the addition and subsequent solvation of the formula amount of tretinoin. The formula amount of gelling agent is added in small quantities under low shear agitation until solvation occurs and the mixture gels. When an acidic carboxy polymer such as Carbopol 934 or Carbopol 940 is used as the gelling agent, the neutralization with an organic amine is accomplished by adding the desired amount of an organic amine after the last portion of the acidic carboxy polymer is added to the mixture and sufficient amount of time allowed for its dispersion. Low shear agitation continues until solvation occurs and the gel is formed.

The procedure preferably should take place at room temperature, i.e. at about 25° C. If desired, additional materials, such as dyes, perfumes, sunscreens, and corticosteroids may be incorporated into the formulations by adding and mixing them with the solvent prior to the addition of the gelling agent.

The following examples are presented to further illustrate compositions of the invention without thereby limiting the scope thereof.

EXAMPLE 1

| | % w/w |
|---|---|
| Tretinoin | 0.001 |
| Butylated hydroxytoluene | 0.01 |
| Hydroxypropyl cellulose | 2.0 |
| Propylene glycol | q.s. to 100.0 |

EXAMPLE 2

| | % w/w |
|---|---|
| Tretinoin | 0.5 |
| Butylated Hydroxyanisole | 0.10 |
| Hydroxypropyl cellulose | 5.00 |
| Propylene glycol | q.s. to 100.0 |

EXAMPLE 3

| | % w/w |
|---|---|
| Tretinoin | 0.05 |
| α-tocopherol | 0.05 |
| Hydroxyethylcellulose | 2.5 |
| Ethanol | q.s. to 100.0 |

EXAMPLE 4

| | % w/w |
|---|---|
| Tretinoin | 0.005 |
| Butylated hydroxytoluene | 0.05 |
| Carbopol 940 | 3.0 |
| β-alanine | 3.0 |
| Ethanol | q.s. to 100.0 |

EXAMPLE 5

| | % w/w |
|---|---|
| Tretinoin | 0.025 |
| Butylated hydroxytoluene | 0.05 |
| Hydroxypropyl cellulose | 3.0 |
| Ethanol | q.s. to 100.0 |

EXAMPLE 6

| | % w/w |
|---|---|
| Tretinoin | 0.025 |
| Butylated hydroxytoluene | 0.05 |
| Carbopol 940 | 3.00 |
| Diisopropanol amine | 3.00 |
| Isopropanol | q.s. to 100.0 |

EXAMPLE 7

| | % w/w |
|---|---|
| Tretinoin | 0.1 |
| Butylated Hydroxyanisole | 0.05 |
| Hydroxyethylcellulose | 4.0 |
| Perfume Oil | 0.25 |
| Dye | 0.25 |
| Ethanol - Isopropanol 50/50 mixture by weight | q.s. to 100.0 |

EXAMPLE 8

| | % w/w |
|---|---|
| Tretinoin | 0.15 |
| α-tocopherol | 0.05 |
| Hydroxypropyl cellulose | 0.5 |
| Hydrocortisone | 0.5 |
| Ethanol - Propylene glycol | |

-continued

| | % w/w |
|---|---|
| 50/50 mixture by weight | q.s. to 100.0 |

EXAMPLE 9

| | % w/w |
|---|---|
| Tretinoin | 0.05 |
| Butylated hydroxytoluene | 0.05 |
| Hydroxypropyl cellulose | 3.00 |
| Propylene glycol/isopropanol 50/50 mixture by weight | q.s. to 100.0 |

EXAMPLE 10

| | % w/w |
|---|---|
| Tretinoin | 0.05 |
| Butylated hydroxytoluene | 0.05 |
| Hydroxypropyl cellulose | 3.00 |
| Propylene glycol/ethanol 50/50 mixture by weight | q.s. to 100.0 |

EXAMPLE 11

| | % w/w |
|---|---|
| Tretinoin | 0.05 |
| Butylated hydroxytoluene | 0.05 |
| Hydroxypropyl cellulose | 3.00 |
| Ethanol/isopropanol 50/50 mixture by weight | q.s. to 100.0 |

EXAMPLE 12

| | % w/w |
|---|---|
| Tretinoin | 0.05 |
| Butylated hydroxytoluene | 0.05 |
| Carbopol 934 | 1.5 |
| β-alanine | 1.5 |
| Propylene glycol/ethanol 50/50 mixture by weight | q.s. to 100.0 |

EXAMPLE 13

| | % w/w |
|---|---|
| Tretinoin | 0.02 |
| Butylated Hydroxytoluene | 0.05 |
| Carbopol 934 | 1.5 |
| Diisopropanol amine | 1.5 |
| Propylene glycol/isopropanol 50/50 mixture by weight | q.s. to 100.0 |

TABLE OF ADDITIONAL EXAMPLES

| Examples | 14 | 15 | 16 | 17 | 18 | 19 | 20 | 21 | 22 | 23 | 24 | 25 |
|---|---|---|---|---|---|---|---|---|---|---|---|---|
| Tretinoin | 0.01 | 0.01 | 0.002 | 0.025 | 0.025 | 0.02 | 0.05 | 0.025 | 0.05 | 0.05 | 0.5 | 0.5 |
| BHT | | | 0.05 | | | | 0.05 | | | | | |
| BHA | | | | 0.05 | | | | | | | | |
| Vitamin C | | 0.05 | | | | | | | | | | |
| Vitamin E | 0.05 | | | | | 0.05 | | 0.05 | 0.05 | 0.05 | | |
| Propyl gallate | | | | | 0.05 | | | | | | 0.05 | 0.10 |
| Propylene glycol | 97.44 | | | | | | 48.40 | | 95.90 | | 25.45 | |
| Ethanol | | | | 48.72 | 97.93 | 95.93 | 95.93 | 50.00 | | | 94.40 | 70.00 | 34.65 |
| Isopropyl alcohol | | 97.44 | 48.72 | | | | | 99.18 | | | | 60.00 |
| Carbopol 934 | | | | | 2.0 | | | | | | | |
| Carbopol 940 | | | | | | 2.0 | | | | | | |
| Hydroxyethylcellulose | 2.0 | | 2.0 | | | | | 0.75 | | 3.5 | | 4.5 |
| Hydroxy propylcellulose | | 2.0 | | 2.0 | | | 0.75 | | 3.0 | | 4.0 | |
| β-alanine | | | | | 2.0 | | | | | | | |
| Diisopropanol amine | | | | | | 2.0 | | | | | | |
| Dye | | | 0.25 | | | | 0.25 | | | | | 0.25 |
| Perfume | 0.25 | 0.25 | | | | | | 0.25 | | | | |
| Hydrocortisone | 0.25 | | 0.25 | | | | 0.25 | | 1.0 | 2.0 | | |

In use, the tretinoin gel composition of the present invention is generally applied daily until the desired relief is obtained. The number of daily applications depends on the severity of the acne condition that the patient has, and may vary between one and three applications. Normally the treatment requires at least 8–12 weeks. However, acne in its mildest form i.e., only a small number of comedones, may be substantially cleared in four to six weeks. More severe cases may require two to three months or longer.

It has been observed in use that the gel formulations of the present invention were easy to apply, remaining on the areas that were treated with little tendency to run and pool or to produce disturbing irritation at the angles of the mouth or nasolabial folds. Furthermore, and quite unexpectedly, only momentary stinging rather than prolonged discomfort, following application, was generally experienced as compared to previously used dosage forms.

Clinical studies have been conducted by different investigators on the relative effectiveness of the gel formulations of the present invention containing tretinoin in combination with butylated hydroxytoluene, hydroxypropyl cellulose and ethanol in comparison to cream formulations containing tretinoin in combination with stearic acid, isopropyl myristate, polyoxy 40 stearate, stearyl alcohol, xanthan gum, sorbic acid, and butylated hydroxytoluene. The studies were double-blind, parallel clinical studies comparing gels and creams having the same concentrations of tretinoin, against each other and against their respective control vehicle or placebo without tretinoin. Tables I through III summarize the combined results of these studies.

Table I compares overall effectiveness data of the identified cream and gel formulations on the treatment of acne whether it be in the form of comedones, pustules, papules, cysts or nodules. Table II compares effectiveness data of creams and gels in reducing comedones. Table III compares effectiveness of creams and gels in reducing papules. It is to be noted that the result should be interpreted in an order-of-magnitude sense and not an absolute sense. The reason for this is the variables affecting the outcome of the result, such as, different investigators, different groups of patients, time, and geographic or climatic factors.

TABLE I

| Tretinoin Strength | Percent of Patients Having a Good or Excellent Clinical Evaluation | | | |
|---|---|---|---|---|
| | Number of Patients* | | Percent | |
| | Cream | Gel | Cream | Gel |
| .000% | 121 | 66 | 28 | 39 |
| .010% | 59 | 41 | 31 | 83 |
| .025% | 65 | 67 | 46 | 83 |
| .050% | 125 | 64 | 62 | 80 |
| .100% | 63 | —** | 70 | —** |

TABLE II

| Tretinoin Strength | Percent Reduction of Comedones | | | |
|---|---|---|---|---|
| | Number of Patients* | | Percent | |
| | Cream | Gel | Cream | Gel |
| .000% | 122 | 60 | 35 | 48 |
| .010% | 62 | 38 | 44 | 67 |
| .025% | 67 | 65 | 44 | 77 |
| .050% | 126 | 62 | 61 | 78 |
| .100% | 63 | —** | 54 | —** |

TABLE III

| Tretinoin Strength | Percent Reduction of Papules | | | |
|---|---|---|---|---|
| | Number of Patients* | | Percent | |
| | Cream | Gel | Cream | Gel |
| .000% | 122 | 60 | 23 | 34 |
| .010% | 62 | 38 | 13 | 62 |
| .025% | 67 | 65 | 52 | 60 |
| .050% | 126 | 62 | 53 | 62 |
| .100% | 63 | —** | 64 | —** |

*Some of the patients in the studies had only comedones and some had only papules, although most patients had both. Therefore, Table I, which summarizes the investigators' evaluation of overall effectiveness, would be expected to show somewhat greater total number of patients than either of Tables II and III, and does so with respect to the "gel" patients. However, one of the investigators, omitted overall evaluation for the "cream" patients, providing only separate evaluation with respect to comedones and pustules. Hence the lower number of total patients in the cream column in Table I as compared to Tables II and III.
**No test was run.

Referring to Tables I, II and III, it is apparent that there is a higher percent improvement in acne conditions when treating patients with a zero strength or placebo gel than with a zero strength or placebo cream. The reason for this difference, no doubt, is in the cleansing or disinfecting nature of the carriers: while both carriers effect reduction of acne conditions due to the cleansing capabilities of some of their components, the gel carrier, having an alcohol, propylene glycol or mixtures of alcohols and propylene glycol therein, exhibits higher antibacterial or cleansing properties.

It is also apparent from Tables I, II and III that the gel formulations of various tretinoin concentration effect unexpectedly greater improvement in reducing acne conditions than do the cream formulations of the same tretinoin concentration. In fact, a ten fold increase in tretinoin concentration is necessary in the cream formulations to achieve the effect of the 0.01% gel formulations both in the reduction of comedones and papules and in overall clinical improvement. As explained previously herein, this is thought to be due to the availability of tretinoin in micro-fine form for absorption through the skin.

As will be obvious to those skilled in the art, many variations and modifications may be made without departing from the spirit and scope of the invention.

What is claimed is:

1. A gel formulation for topical application comprising from about 0.01% to about 0.025% by weight of said formulation of tretinoin; and a vehicle system consisting essentially of (a) from about 84 to about 99% by weight of said formulation of an organic solvent selected from the group consisting of ethanol, isopropanol, and propylene glycol; (b) an effective amount to inhibit oxidation of said tretinoin of a pharmaceutically acceptable antioxidant soluble in said organic solvent; and (c) an effective amount to cause gelling of hydroxypropyl cellulose.

2. The product of claim 1 wherein the antioxidant is selected from the group consisting of butylated hydroxyanisole, butylated hydroxytoluene, α-tocopherol, ascorbic acid, and propyl gallate.

3. The product of claim 2 which contains from about 0.01 to about 0.10% by weight of said antioxidant and from about 0.5 to about 5.0% by weight of said hydroxypropyl cellulose.

4. The product of claim 1 wherein said organic solvent comprises a mixture selected from the group consisting of ethanol and propylene glycol; isopropanol and proplyene glycol; and ethanol and isopropanol.

5. The product of claim 1 further comprising a dye.

6. The product of claim 1 further comprising a perfume oil.

7. The product of claim 1 further comprising a sunscreen.

8. The product of claim 1 further comprising an antimicrobial.

9. The product of claim 1 further comprising a topical corticosteroid.

10. A gel formulation for topical treatment of acne vulgaris consisting essentially of:
from about 0.01 to about 0.025% by weight of tretinoin;
from about 84 to about 99% by weight of an organic solvent selected from the group consisting of ethanol, isopropanol, propylene glycol and mixtures thereof;
from about 0.025 to about 0.075% by weight of an antioxidant selected from the group consisting of butylated hydroytoluene, butylated hydroxyanisole, ascorbic acid, propyl gallate, and α-tocopherol;
and from about 0.5 to about 3.0% of hydroxypropyl cellulose.

* * * * *